United States Patent
Beutler et al.

[11] Patent Number: 5,972,393
[45] Date of Patent: Oct. 26, 1999

[54] PREPARATION OF DEHYDRATION ACIDIFIED MILK PRODUCT

[75] Inventors: Ernst Beutler, Emmenmatt; Leuka Favre-Galliand, Lausanne; Johann Illi, Heimberg, all of Switzerland; Andreas Sutter, Yorba Linda, Calif.

[73] Assignee: Nectec S.A., Veyvey, Switzerland

[21] Appl. No.: 07/965,202

[22] Filed: Oct. 23, 1992

[30] Foreign Application Priority Data

Oct. 25, 1991 [CH] Switzerland ................. 03 129/91-2

[51] Int. Cl.$^6$ ................................................. A23L 9/12
[52] U.S. Cl. .................. 426/34; 426/580; 426/583; 426/588; 426/800; 426/801
[58] Field of Search .................. 426/34, 41, 42, 426/43, 580, 583, 585, 586, 587, 588, 800, 801

[56] References Cited

U.S. PATENT DOCUMENTS

| | | | |
|---|---|---|---|
| 1,450,836 | 4/1923 | Bosworth | 426/801 |
| 1,882,638 | 10/1932 | Johnson et al. | 426/801 |
| 4,399,220 | 8/1983 | Smiley | 435/139 |
| 4,435,432 | 3/1984 | Klupsch | 426/43 |
| 4,588,595 | 5/1986 | Okonogi et al. | 426/43 |
| 4,855,147 | 8/1989 | Yokota et al. | 426/43 |

FOREIGN PATENT DOCUMENTS

| | | |
|---|---|---|
| 2073279 | 10/1971 | France . |
| 1692456 | 8/1971 | Germany . |
| 1512890 | 6/1978 | United Kingdom . |

OTHER PUBLICATIONS

Nakayama, 02–268644, Nov. 1990, Patent Abstracts of Japan, abstract only.

Derwent Abstract AN 90–371973 of Japanese Patnet Application No. JP–A–2 268 644, Nov., 1990.

Broome, et al. "The Use of Cheese Whey Protein Concentrate in the Manufacture of Skim Milk Yogurt". *The Australian Journla of Dairy Technology*. 37(4): 1982; pp. 139–142.

Raŝić, et al. "Yoghurt: Scientific Grounds, Technology, Manugfacture and Preparations". *Fermented Fresh Milk Products*. vol. 1, 1978; pp. 50–52, 103–104.

Anonymous. "Dried Yogurt Product". *Food Technology*. 32(11): 1978; p. 69.

*Primary Examiner*—Leslie Wong
*Attorney, Agent, or Firm*—Voit & O'Donnell, LLP

[57] ABSTRACT

A dehydrated acidified milk product is made by preparing an aqueous composition containing milk protein and having a dry matter content of from 10% to 40% by weight. The aqueous composition is inoculated with a strain of *L. helveticus* which exclusively forms lactic acid L(+) and a strain of *S. thermophilus* and fermented to obtain a fermented composition having a pH of from 4 to 5. The fermented composition is dried to obtain the dehydrated acidified product.

21 Claims, No Drawings

PREPARATION OF DEHYDRATION ACIDIFIED MILK PRODUCT

BACKGROUND OF THE INVENTION

This invention relates to a process for the production of a dehydrated acidified milk and to the milk obtained by this process.

It is known that an acidified milk, such as a yogurt, for example in the form of a gel or beverage, can have a beneficial effect on the health.

In this connection, French patent No. 2 506 129 (EVOG) recalls the fact that, in the traditional combinations of microorganisms used to make yogurt, *Lactobacillus bulgaricus* is distinguished in particular by the formation of flavour, rapid acidification and the formation of lactic acid D(-) while *Streptococcus thermophilus* is distinguished in particular by the formation of a consistent gel, slow acidification and the formation of lactic acid L(+). To produce an analogous consistent gel, this patent proposes the *Bifidobacterium longum* strain DSM 2054, which is distinguished by the formation of lactic acid L(+) and which was selected for its exceptional acidifying power.

British Patent Specification No. 1,512,890 (YAKULT HONSHA K.K.) describes the production of an acidified milk beverage by fermentation with a combination of a strain of *Lactobacillus helveticus* capable of rapidly producing lactic acid and a strain of *Lactobacillus casei* which produces very little acid, the strains being selected so that their combination results in rapid acidification without producing any diacetyl or other secondary product which would provide the end product with an undesirable flavour.

U.S. Pat. No. 4,399,220 (Smiley) recalls that *Lactobacillus helveticus*, more particularly *L. helveticus* subspecies *jugurti*, is traditionally used in the production of hard cheeses. This US patent proposes a process for the production of a culture of such a microorganism of which the acidifying power remains particularly stable.

SUMMARY OF THE INVENTION

The problem addressed by the present invention was to provide a process for the production of a dehydrated acidified milk which could be carried out on an industrial scale, which would enable relatively low pH values to be reached without causing any separation of proteins and which give a product distinguished in particular by its good keeping properties and its favourable effects on the health of the consumers for which it is intended, particularly young children and babies.

To this end, in the process for the production of a dehydrated acidified milk according to the invention, an aqueous solution or emulsion is prepared with a dry matter content of 10 to 40% and a composition similar to that of milk, the solution is fermented to a pH of 4.0 to 5.0 with a combination of at least one strain of *Streptococcus thermophilus* and a strain of *Lactobacillus helveticus* exclusively forming lactic acid L(+) and the solution is dried to a water content below 3% by weight.

It has been found that this process can be effectively carried out on an industrial scale without any risk of protein separation and the problems it causes in spite of the relatively low pH value reached during the fermentation step. Similarly, the product obtained by this process has good keeping properties, it does not undergo any changes in its organoleptic qualities, particularly after storage for 12 to 24 months at a temperature of 20 to 27° C. in an inert gas atmosphere, for example of $CO_2$ arid/or $N_2$, in hermetically sealed lacquered tin cans, and is effectively capable of exerting favourable effects on the health of the consumers for which it is intended.

DETAILED DESCRIPTION OF THE INVENTION

The process according to the invention may be carried out using any starting materials capable of combining the components which, together, form a composition similar to that of a milk, such as cow's milk or human milk.

A first preferred embodiment of the process according to the invention comprises preparing an aqueous solution having a dry matter content of 15 to 40% by weight and a composition similar to that of a whole or skimmed cow's milk, for example optionally containing an added lactic and/or vegetable fat, such as butter oil, corn oil and/or coconut oil, and carbohydrates such as, for example, maltodextrin, sucrose, starch and/or lactose. To this end, it is possible to reconstitute a powder-form cow's milk or to concentrate a cow's milk to the desired dry matter content and optionally to add the fat and/or carbohydrates mentioned above.

A solution of the type in question may contain proteins consisting of 75 to 82% by weight case:in and 18 to 25% by weight whey proteins.

The solution is preferably spray-dried after fermentation to a pH value of 4.0 to 5.0.

A second preferred embodiment of the process according to the invention comprises preparing an aqueous solution having a dry matter content of 10 to 40% by weight and a composition adapted to the needs of babies. To this end, it is possible to combine the components such as a first fraction of mineral salts, acid casein or potassium caseinate, serum proteins, cream and/or corn oil and milk powder, more particularly in ratios designed to simulate the composition of human milk, optionally to add carbohydrates, such as for example maltodextrin, sucrose, starch and/or lactose, and to reconstitute the whole to the desired dry matter content, for example by mixing with softened water. The solution may be homogenized at this stage, more particularly in one or two steps, for example under a pressure of 50 to 200 bar.

The solution thus formed may contain proteins consisting of 40 to 82% by weight casein and 18 to 60% by weight whey proteins.

After the solution has been fermented to a pH value of 4.0 to 5.0, it is preferably concentrated to a dry matter content of 40 to 55% by weight by evaporation in vacuo and supplemented with vitamins and, optionally, a second fraction of mineral salts and then spray-dried. This optional second fraction of mineral salts may comprise in particular salts of Ca and Mg which are preferably added after evaporation and either before or even during or after drying.

It has been found that it can also be of advantage to add lecithin either during the initial mixing or after evaporation and before drying. Finally, optional carbohydrates may also be added after drying rather than during the initial mixing, particularly in hot climates where there is a risk of problems caused by sticking in the drying nozzle.

In each preferred embodiment of the process according to the invention, the solution is fermented by inoculation with, preferably, 1 to 5% by volume of a culture or mixture of cultures containing $10^7$ to $10^9$ germs of at least one *S.* thermophilus and $10^7$–$10^9$ germs of *L. helveticus* per ml and incubation for 2 to 15 h at a temperature of 37 to 45° C.

This fermentation may be carried out dicontinuously, i.e. in batches, or continuously. Thus, in one advantageous embodiment of the process according to the invention which is particularly suitable for application on an industrial scale, fermentation is carried out continuously in two successive steps. In the first of these steps, incubation may be carried out for 0.5 to 5 h to pH 5.0 to 6.0 and preferably to pH 5.1 to 5.7 at a temperature of 37 to 45° C. In the second of these steps, incubation may be carried out for 1 to 10 h to pH 4.0 to 5.0 and preferably to pH 4.5 to 4.8 at a temperature of 37 to 45° C.

These fermentation steps may be carried out in two successive fermenters on a continuous production line, the volume of solution treated in each fermenter being proportional to the desired residence time for example.

This method of operation lends itself particularly well to optimal work of each of the two microorganisms forming the combination in symbiosis, the first fermentation step favouring in particular the work of the *S. thermophilus* strain(s) and the second step favouring in particular the work of the *L. helveticus* strain.

In each embodiment of the process according to the invention, the *S. thermophilus* strain(s) may be selected, for example, from the strains marketed for the production of yogurts or isolated from yogurts. The *L. helveticus* strain may be selected for its ability to exclusively form lactic acid L(+), for example from the strains marketed for the production of cheese or acidifed milk or isolated from cheeses or acidified milks.

Among various strains thus selected, three were lodged by way of example under the Budapest Treaty on 15.10.91 in the Collection Nationale de Cultures de microorganismes (CNCM), Institut Pasteur, 28 rue du Dr. Roux, 75724 Paris, Cedex 15, France, where they were given the numbers CNCM I-1154, CNCM I-1155 and CNCM I-1156.

Details of their morphology and properties are shown below:

Morphology

Examined under a microscope, these strains are in the form of relatively long and thin rodlets.

They are microaerophilic gram-positive bacteria which do not form spores.

Metabolism

These bacteria produce homolactic fermentation with formation of lactate as the end product.

Various tests with each of them give the following results: catalase activity (−), production of carbon dioxide (−), coagulation of milk (+), hydrolysis of arginine (−)

They ferment the following sugars:

|  | CNCM I-1154 | CNCM I-1155 | CNCM I-1156 |
| --- | --- | --- | --- |
| L-Arabinose | − | − | − |
| D-Xylose | − | − | − |
| D-Glucose | + | + | + |
| D-Mannose | + | − | + |
| D-Fructose | + | − | − |
| Galactose | + | + | + |
| Lactose | + | + | + |
| Maltose | − | − | − |
| Sucrose | − | − | − |
| Trehalose | − | − | − |
| Raffinose | − | − | − |

-continued

|  | CNCM I-1154 | CNCM I-1155 | CNCM I-1156 |
| --- | --- | --- | --- |
| Salicine | − | − | − |
| Cellobiose | − | − | − |
| D-Sorbitol | − | − | − |
| D-Mannitol | − | − | − |
| Inositol | − | − | − |
| Cellobiose | − | − | − |
| Glycerine | − | − | − |
| Starch | − | − | − |

Growth Medium

These strains may be grown on MRS medium or reconstituted skimmed milk containing 10% dry matter. The optimal temperature is 40–45° C. The pH after 24 h in reconstituted skimmed milk is approx. 3.40.

Feature

These three strains exclusively (>99%) produce lactic acid L(+).

The present invention also relates to the product obtained by the process according to the invention. This product is intended in particular for young children and babies on whose health it can exert a beneficial effect, particularly in preventing diarrhoea, by comparison with comparable traditional products.

In one particular embodiment of the product, a lyophilized culture of Bifidobacterium may also be added.

EXAMPLES

The following Examples are intended to illustrate the process and the product according to the invention. Various tests are also described to illustrate the qualities of the product. In the Examples and tests, percentages are by weight unless otherwise indicated.

Example 1

Corn oil, sucrose, maltodextrin and starch are added to a whole cow's milk so that the solution obtained has the following composition (in % by weight, based on dry matter):

| Milk fats | 18.2 |
| --- | --- |
| Corn oil | 4.6 |
| Milk proteins (including approx. 80% casein and approx. 20% whey proteins) | 14.5 |
| Lactose | 21.2 |
| Sucrose | 15.5 |
| Maltodextrin | 16.5 |
| Starch | 6.2 |
| Minerals | 3.2 |

This solution is concentrated to 33% dry matter by evaporation in vacuo.

The concentrated solution is inoculated with 5% by volume of a culture containing per ml approximately $10^8$ germs of a commercial *Streptococcus thermophilus* and approximately $10^8$ germs of the *Lactobacillus helveticus* strain CNCM I-1154. The concentrated solution may be fermented for about 12.5 h at 43° C. to a pH value of 4.2 to 4.3. The fermented solution is spray-dried.

A dehydrated acidified milk, i.e. an acidified milk powder, intended in particular for young children is obtained and may be reconstituted with water in a quantity of approximately 140 g powder to approximately 900 ml water. This powder has a residual water content of approximately 2% and keeps without changing for at least 12 months at 27° C. in hermetically sealed lacquered tin cans.

Example 2

The procedure is as described in Example 1 except that the concentrated solution is inoculated with the *Lactobacillus helveticus* strain CNCM I-1155 instead of the strain CNCM I-1154.

The dehydrated acidified milk obtained is comparable in its properties with the product obtained in Example 1.

Example 3

The procedure is as described in Example 1, except that the concentrated solution is inoculated with the *Lactobacillus helveticus* strain CNCM I-1156 instead of strain CNCM I-1154.

The dehydrated acidified milk obtained is comparable in its properties with the product obtained in Example 1.

Test 1

The dehydrated acidified milk obtained in Example 1 is subjected to a microbial proliferation test in a feeding bottle.

To this end, the dehydrated acidified milk is reconstituted with water in a quantity of 139 g powder to 900 ml water and is inoculated with various pathogenic microorganisms.

For comparison, a reconstituted non-acidified dehydrated milk adapted in its composition to the needs of babies is inoculated with the same microorganisms.

The pathogenic microorganisms used are *Salmonella typhimurium, Escherichia coli, Staphylococcus aureus* and *Bacillus cereus*. They are inoculated in a quantity of $10^4$–$10^5$ german per ml reconstituted milk. The respective populations are counted after incubation for 8 h at 37° C. The results obtained are set out in Table 1 below:

TABLE 1

Microbial proliferation test in a feeding bottle
(initial inoculation with $10^4$–$10^5$ germs/ml - incubation for 8h at 37° C).

| Product tested | S. typhi-murium | E. coli | St. aureus | B. cereus |
| --- | --- | --- | --- | --- |
| Non-acidified comparison sample | $4.2 \cdot 10^7$ | $9.1 \cdot 10^7$ | $8.0 \cdot 10^6$ | $8.0 \cdot 10^6$ |
| Acidified de-hydrated milk acc. to Ex. 1 | <10 | <10 | $2.2 \cdot 10^3$ | $2.3 \cdot 10^4$ |

Accordingly, it can be seen that the acidified dehydrated milk obtained in Example 1 completely inhibits the growth of *Staph. aureus* and *B. Cereus* and even inactivates *S. typhimurium* and *E. coli*.

Example 4

A first fraction of mineral salts, potassium caseinate, demineralized whey proteins, cream, skimmed milk powder, maltodextrin and softened water are mixed to obtain a solution having a dry matter content of 20% by weight and the following composition (in % by weight, based on dry matter):

| | |
| --- | --- |
| Milk fats | 19.4 |
| Corn oil (subsequently added hot) | 4.8 |
| Lecithin (subsequently added hot) | 0.5 |
| Milk proteins (50% casein, 50% whey proteins) | 12.9 |
| Lactose | 45.4 |
| Maltodextrin | 15.0 |
| Minerals (including Ca and Mg added before, during or after drying) | 2.0 |

After preheating to 80° C., the corn oil is added. The solution is heat-treated by injection of steam at 125° C. for 5 s. The solution is then homogenized under a pressure of 75 bar at 43° C. The homogenized solution or emulsion is then inoculated with 2% by volume of a culture containing per ml approx. $10^8$ germs of a commercial *Streptococcus thermophilus* and approx. $10^8$ germs of the *Lactobacillus helveticus* strain CNCM I-1154.

The solution is fermented for 4.5 h at 43° C. to a pH value of 4.2 to 4.3 and is then cooled to 10° C.

The solution is then preheated to 75° C. and concentrated by evaporation to 48% dry matter. Lecithin is added. A second fraction of mineral salts, namely salts of Ca and Mg, is then added and the solution is spray-dried.

A dehydrated acidified milk, i.e. an acidified milk powder, intended in particular for babies is obtained and may be reconstituted with water in a quantity of 135 g powder to approx. 900 ml water. The powder has a residual water content of approximately 2% and keeps without changing for at least 12 months at 27° C. in hermetically sealed lacquered tin cans.

Example 5

The procedure is as described in Example 4, except that the solution or emulsion is inoculated with the *Lactobacillus helveticus* strain CNCM I-1155 instead of strain CNCM I-1154.

The dehydrated acidified milk obtained is comparable in its propertes with the product obtained in Example 4.

Example 6

The procedure is as described in Example 4, except that the solution or emulsion is inoculated with the *Lactobacillus helveticus* strain CNCM I-1156 instead of strain CNCM I-1154.

The dehydrated acidified milk obtained is comparable in its propertes with the product obtained in Example 4.

Test 2

The dehydrated acidified milk obtained in Example 4 is subjected to a microbial proliferation test in a feeding bottle.

To this end, the dehydrated acidified milk is reconstituted with water in a quantity of 134 g powder to 900 ml water and inoculated with various pathogenic microorganisms in the same way as described above in test 1.

Table 2 below shows the results obtained after incubation for 8 h at 37° C. against the results obtained for comparison with a sample of reconstituted dehydrated milk similar in composition, but not acidified.

TABLE 2

Microbial proliferation test in a feeding bottle
(initial inoculation with $10^4$–$10^5$ germs/ml - incubation for 8h at 37° C).

| Product tested | S. typhimurium | E. coli | St. aureus | B. cereus |
| --- | --- | --- | --- | --- |
| Non-acidified comparison sample | $4.2 \cdot 10^7$ | $9.1 \cdot 10^7$ | $8.0 \cdot 10^6$ | $8.0 \cdot 10^6$ |
| Acidified dehydrated milk acc. to Ex. 4 | 10 | 10 | $1.3 \cdot 10^4$ | $1.9 \cdot 10^4$ |

Accordingly, it can be seen that the acidified dehydrated milk obtained in Example 4 completely inhibits the growth of these four pathogenic microorganisms and even inactivates S. typhimurium and E. coli.

Test 3

An acceptance study was carried out on the acidified dehydrated milk obtained in Example 4.

The study involves 25 babies during the first three months of their lives. The development of their size and weight is followed and the regurgitations, the frequency of stools and their consistency are recorded.

Growth curves established from the results of this study are situated right in the middle of the ranges considered as normal in Europe and show a slightly more pronounced slope than a typical average curve.

The results of monitoring of the regurgitations and stools are set out in Table 3 below which shows the average quantities of milk consumed per day in ml per kg baby (values in brackets) and the percentage of babies in which the number of regurgitations is below 2 per day and of which the frequency and consistency of the daily stools correspond to the numbers and descriptions indicated.

TABLE 3

Acceptance test of the acidified dehydrated milk according to Example 4 in babies

|  | First month | Second month | Third month |
| --- | --- | --- | --- |
| Consumption of milk (ml/kg) | 175 (120–243) | 160 (107–203) | 142 (85–181) |
| Regurgitations <2 | 86 | 94 | 93 |
| Frequency of stools |  |  |  |
| <1 | 4 | 10 | 18 |
| 1–3 | 83 | 80 | 70 |
| <4 | 13 | 10 | 12 |
| Consistency of stools |  |  |  |
| firm | 63 | 54 | 50 |
| soft | 33 | 32 | 35 |
| liquid | 4 | 14 | 15 |

The results reflect an excellent tolerance of the dehydrated acidified milk by the babies and a relatively low tendency towards regurgitation.

Example 7

A first fraction of mineral salts, potassium caseinate, demineralized whey proteins, cream, skimmed milk powder, maltodextrin and softened water are continuously mixed to obtain 4000 litres per hour of a solution having a dry matter content of 20% by weight and the following composition (in % by weight, based on dry matter):

| Milk fats | 19.2 |
| --- | --- |
| Corn oil (subsequently added hot) | 5.3 |
| Lecithin (subsequently added hot) | 0.5 |
| Milk proteins (50% casein, 50% whey proteins) | 12.8 |
| Lactose | 45.7 |
| Maltodextrin | 14.6 |
| Minerals (including Ca and Mg added before, during or after drying) | 1.9 |

The solution is continuously preheated to 80° C. in a plate-type heat exchanger. Corn oil is added. The solution is then heat-treated by injection of steam at 125° C. for 5 s. The solution is homogenized in two steps at 43° C., the first under a pressure of 150 bar and the second under a pressure of 50 bar. The homogenized solution or emulsion is inoculated with 1% by volume of a culture containing per ml approx. $5.10^8$ germs of two commercial Streptococcus thermophilus strains and 3% by volume of a culture containing per ml approx. $2.10^8$ germs of the Lactobacillus helveticus strain CNCM I-1154.

The solution is fermented first for about: 1 h at 42° C. to pH 5.5 in a 4000 l fermenter and then for about 1.5 h at 42° C. to pH 4.7 in a 6000 l fermenter. The solution is preheated to 75° C. in a plate-type heat exchanger. It is then concentrated by evaporation to a dry matter content of 50% in a three-stage falling-film evaporator. The lecithin is then added. A second fraction of mineral salts, namely salts of Ca and Mg, is added and the solution is then spray-dried.

A dehydrated acidified milk, i.e. an acidified milk powder, intended in particular for babies is continuously obtained and may be reconstituted with water in a quantity of approx. 134 g powder to approximately 900 ml water. The powder has a residual water content of approximately 2% and keeps without changing for at least 12 months at 27° C. in hermetically sealed lacquered tin cans.

Example 8

The procedure is as described in Example 7, except that the solution or emulsion is inoculated with the Lacto bacillus helveticus strain CNCM I-1155 instead of the strain CNCM I-1154 and the second fraction of mineral salts is not added until after spray drying.

The dehydrated acidified milk obtained is comparable in its properties with the product obtained in Example 7.

Example 9

The procedure is as described in Example 7 except that the solution or emulsion is inoculated with the Lactobacillus helveticus strain CNCM I-1156 instead of the strain CNCM I-1154. The dehydrated acidified milk obtained is comparable in its properties with the product: obtained in Example 7.

Example 10

A lyophilized commercially available Bifidobacterium is added to the product obtained in any of Examples 4 to 9 in such a quantity that the powder has a content of approx. $5.10^7$ Bifidobacterium germs per g.

We claim:

1. A process for preparing a dehydrated acidified milk product comprising:

preparing an aqueous composition containing milk proteins and having a dry matter content of from 10% to 40% by weight;

inoculating the aqueous composition with a strain of *L. helveticus* which exclusively forms lactic acid L(+) and a strain of *S. thermophilus* and fermenting the inoculated composition to obtain a fermented composition having a pH of from 4 to 5; and drying the fermented composition to obtain a dehydrated acidified milk product.

2. A process according to claim 1 wherein the strain of *L. helveticus* is selected from the group consisting of *L. helveticus* CNCM I-1154, *L. helveticus* CNCM I-1155 and *L. helveticus* CNCM I-1156.

3. A process according to claim 1 wherein the aqueous composition has a dry matter of from 15% to 40% by weight.

4. A process according to claim 1 further comprising concentrating the fermented composition by evaporation in vacuo prior to drying.

5. A process according to claim 1 wherein the milk proteins in the aqueous composition comprise 75% to 82% by weight casein and 18% to 25% by weight whey proteins.

6. A process according to claim 5 wherein the aqueous composition comprises a concentrated cow's milk.

7. A process according to claim 5 wherein the aqueous composition comprises a reconstituted powder-form cow's milk.

8. A process according to claim 6 wherein the aqueous composition further comprises lactic fat, vegetable fat or carbohydrates.

9. A process according to claim 7 wherein the aqueous composition further comprises lactic fat, vegetable fat or carbohydrates.

10. A process according to claim 1 wherein the milk proteins in the aqueous composition comprise 40% to 82% by weight casein and 18% to 60% by weight whey proteins.

11. A process according to claim 10 wherein the aqueous composition comprises mineral salts, acidic casein or potassium caseinate, whey proteins, cream and milk powder.

12. A process according to claim 11 further comprising concentrating the fermented composition by evaporation in vacuo prior to drying.

13. A process according to claim 12 wherein the fermented composition is concentrated to a dry matter content from 40% to 55% by weight.

14. A process according to claim 12 further comprising adding mineral salts to the fermented composition after concentrating.

15. A process according to claim 1 further comprising adding a lyophilized culture of Bifidobacterium to the dehydrated product.

16. A process according to claim 1 wherein the fermented composition is dried by spray drying.

17. A process according to claim 1 wherein the fermented composition is dried to a water content below 3% by weight.

18. A process according to claim 1 wherein the aqueous composition is inoculated with 1% to 5% by volume of a culture containing $10^7$–$10^9$ germs/ml *S. thermophilus* and $10^7$–$10^9$ germs/ml *L. helveticus* and wherein the inoculated composition is fermented for 2 hours to 15 hours at 37° C. to 45° C.

19. A process according to claim 1 wherein the aqueous composition is inoculated with 1% to 5% by volume of a culture containing $10^7$–$10^9$ germs/ml *S. thermophilus* and $10^7$–$10^9$ germs/ml *L. helveticus* and wherein the inoculated composition is fermented at 37° C. to 45° C. for from 0.5 hour to 5 hours to a pH of from 5.0–6.0 and for from 1 hour to 10 hours to a pH of from 4.2 to 5.0.

20. A dehydrated milk product obtained by the process of claim 1.

21. A dehydrated milk product obtained by the process of claim 2.

* * * * *

UNITED STATES PATENT AND TRADEMARK OFFICE
CERTIFICATE OF CORRECTION

PATENT NO. : 5, 972, 393
DATED : October 26, 1999
INVENTOR(S) : Ernst BEUTLER, *et al.*

It is certified that error appears in the above-identified patent and that said Letters Patent is hereby corrected as shown below:

On the title page, left column, in the title (Item [54]), delete "DEHYDRATION" and insert therefor -- DEHYDRATED --.

Column 1, line 1, delete "DEHYDRATION" and insert therefor -- DEHYDRATED --.

Column 9, text line 19 (line 2 of claim 3), after "matter", insert -- content --.

Signed and Sealed this

Third Day of April, 2001

*Attest:*

NICHOLAS P. GODICI

*Attesting Officer*     *Acting Director of the United States Patent and Trademark Office*